(12) United States Patent
Heinonen et al.

(10) Patent No.: US 7,992,555 B2
(45) Date of Patent: Aug. 9, 2011

(54) ANESTHESIA VENTILATOR SYSTEM INCLUDING MANUAL VENTILATION

(75) Inventors: Erkki Heinonen, Helsinki (FI); Leif Brömster, Solna (SE)

(73) Assignee: General Electric Company, Schenectady, NY (US)

( * ) Notice: Subject to any disclaimer, the term of this patent is extended or adjusted under 35 U.S.C. 154(b) by 1041 days.

(21) Appl. No.: 11/564,865

(22) Filed: Nov. 30, 2006

(65) Prior Publication Data
US 2007/0125377 A1    Jun. 7, 2007

(51) Int. Cl.
*F16K 31/02* (2006.01)
*A62B 9/02* (2006.01)

(52) U.S. Cl. .............................. 128/204.21; 128/205.24

(58) Field of Classification Search ........... 128/205.12–203.14, 203.24, 203.25, 128/203.28, 203.29, 204.18, 204.21–204.23, 128/204.28, 205.13, 205.14, 205.24, 207.16
See application file for complete search history.

(56) References Cited

U.S. PATENT DOCUMENTS

| 5,497,767 A * | 3/1996 | Olsson et al. ............ 128/205.13 |
| 7,073,502 B2 | 7/2006 | Bromster |
| 2001/0029946 A1 | 10/2001 | Kitten |

FOREIGN PATENT DOCUMENTS

| EP | 86/05992 | 4/1986 |
| EP | 0621049 A1 | 10/1994 |
| WO | 2004/067055 A2 | 8/2004 |

* cited by examiner

*Primary Examiner* — Kristen C Matter
(74) *Attorney, Agent, or Firm* — Andrus, Sceales, Starke & Sawall, LLP

(57) ABSTRACT

A ventilation system for intensified breathing that includes both a manual ventilation system and automatic ventilation system. The gas mixture from a gas supply system is supplied to a switching valve that is operable between a manual position and an automatic position. When the switching valve is in the manual position, the inhalation gas from the supply system is guided to a manual ventilation bag. When the ventilation bag is squeezed during manual inhalation, the gas flow from the manual bag is directed to the inhalation limb of the patient circuit. When the manual ventilation bag is released, the pressure within the ventilation bag falls below the exhalation pressure, thereby indicating the beginning of the exhalation phase and the re-inflation of the manual ventilation.

10 Claims, 2 Drawing Sheets

ANESTHESIA VENTILATOR SYSTEM INCLUDING MANUAL VENTILATION

BACKGROUND OF THE INVENTION

The present invention generally relates to a ventilation system for use in intensified breathing. More specifically, the present invention relates to an anesthesia ventilation system used during surgical operations where anesthesia is being delivered to a patient through an intravenous line where the ventilation system includes both an automatic ventilation system and a manual ventilation system.

Presently, anesthesia machines are optimized for delivering anesthesia to a patient using volatile anesthetic agent liquids. In such systems, the anesthetic agent is vaporized and mixed into the breathing gas stream in a controlled manner to provide a gas mixture for anesthetizing the patient for a surgical operation. The most common volatile anesthetic agents are halogenated hydrocarbon chains, such as halothane, enflurane, isoflurane, sevoflurane, and desflurane. Additionally, nitrous oxide ($N_2O$) can be counted in this group of volatile anesthetic agents, although the high vapor pressure of nitrous oxide causes nitrous oxide to vaporize spontaneously in the high pressure gas cylinder, where it can be directly mixed with oxygen. The anesthetizing strength of nitrous oxide is seldom enough to anesthetize a patient and therefore is typically mixed with another volatile agent.

Since volatile anesthetic agents are expensive and environmentally damaging to the atmospheric ozone layer, anesthesia machines have been developed to minimize the use of these gases. To keep patients anesthetized, a defined brain partial pressure for the anesthetic agent is required. This partial pressure is maintained by keeping the anesthetic agent partial pressure in the lungs adequate. During steady state, the lung and body partial pressures are equal, and no exchange of anesthetic agent occurs between the blood and the lungs. However, to provide oxygen and eliminate carbon dioxide, continuous lung ventilation is required.

Anesthesia machines designed to deliver volatile anesthetic agents are designed to provide oxygen to the patient and eliminate carbon dioxide, while preserving the anesthetic gases. These goals are typically met using a re-breathing circuit, where exhaled gas is reintroduced into the inhalation limb leading to the patient. In such a re-breathing circuit, carbon dioxide is absorbed from the expired gases by soda-lime in a carbon dioxide absorber. Before inhalation by the patient, the inhalation gas is supplied with additional oxygen and vaporized in aesthetic agents based upon the patient demand. In this arrangement, the additional gas flow added to the re-breathing circuit can be less than 0.5 L/min although the patient ventilation may be 5-10 L/min. The over-pressure inspiration is typically carried out using a ventilator, which is gas driven and utilizes a bag-in-bottle construction. In these ventilators, patient gas is pressurized through separate, flexible rubber membranes from the ventilator gas drive, thereby keeping the ventilator clean and prevent contamination of the re-circulating gases.

Intravenously administered drugs provide an alternative to the volatile anesthetic agents. When intravenous anesthesia is utilized, the primary functionality of the anesthesia machine is no longer needed, since the vaporized anesthetic agent is no longer circulating with the breathing gases. When intravenously administered anesthetic drugs are utilized, the anesthesia machine may use an open breathing circuit where a mixture of fresh oxygen and nitrogen is provided at the rate required by the patient and the expired gases can be removed from circulation. In such an open system, carbon dioxide absorption is no longer needed since re-circulation has been eliminated. Further, the isolation between the patient gases and the drive gases are no longer needed when the ventilation gases are provided directly to the patient. Thus, an anesthesia ventilator optimized for intravenous anesthesia lacks a bag-in-bottle unit and a carbon dioxide absorber. Further, a vaporizer for the volatile anesthetic agents is also no longer needed. These simplifications reduce equipment size, eliminate much of the cleaning requirements by reducing the number of contaminated components, and streamline the manufacturing process.

The applicants' published PCT application WO 2004/067055 describes an open circuit ventilator that includes a manual ventilation feature. The open circuit ventilator is designed to be independent of any electrical power supply. For this reason, a dedicated pressure sensitive manual bag fill valve is included in the ventilation circuit to control the manual bag filling. The manual bag fill valve includes large surface area membranes and an access opening for connecting the sides of the membrane for differential pressure sensing. As stated, the manual bag fill valve controls the bag filling independent of the electrical power supply. However, since most modern open-circuit ventilators are already highly dependent upon the availability of an electrical power supply and include battery backup, the electrical power-free operation is not required in most cases.

Therefore, a need currently exists for a ventilator optimized to be used with intravenous anesthesia that utilizes an open breathing system similar to current ventilators used in intensive care. Further, a need exists for an anesthesia ventilator that includes the ability to manually ventilate the patient, such as during induction and wakeup. The present invention eliminates the need for a manual bag filling valve while providing the manual ventilation functionality to an open-circulation ventilator for optimizing the ventilator for intravenously infused anesthesia applications.

SUMMARY OF THE INVENTION

The present invention is directed to a ventilation system for use in intensified breathing, and particularly for use whenever anesthesia is being delivered to a patient through an intravenous line.

Ventilators using open breathing circuits are typically used in intensive care environments. These ventilators mix breathing gas from oxygen and air sources, provide tidal inspiration with the required gas mixture and regulate expiration pressure for required end-expiratory pressure (PEEP). The ventilation system of the present invention includes both an automatic ventilation system and a manual ventilation system that can be alternatively selected by an operator to control the source of ventilation gases being supplied to the patient. The present invention utilizes already existing functionality provided by open-circuit ventilators and supplements the ventilator with the possibility for manual ventilation. This function is achieved by directing the mixed gas flow to a manual breathing system, where the mixed gas flow is then further directed to the patient with manual ventilation action. Specifically, the mixed inhalation gas from the ventilator is directed through a switching valve such that the gas can be supplied either directly to the patient in an auto-ventilation mode or to a manual ventilation bag during a manual ventilation mode.

When the ventilation system is in the manual ventilation mode, the ventilator gas flow controls are programmed to fill the manual bag. The system utilizes a pressure sensor to monitor the instantaneous pressure within the manual bag. The ventilation system is programmed to fill the manual bag to the required PEEP pressure. However, due to the mass of the manual bag, pressure must be maintained within the bag to keep it open. Therefore, a minimum manual bag overpressure above ambient of approximately 2 cm $H_2O$ is required to keep the bag open.

When the ventilation system is in the manual mode, the manual bag can be squeezed until the pressure within the bag (Pbag) rises over the PEEP pressure for the patient. Because the PEEP pressure represents the prevailing pressure in the patient's lungs at the end of the previous exhalation, the increase in the bag pressure over the PEEP pressure upon compression causes the gas to flow into the patient's lungs from the manual bag. When the manual bag is released, the pressure within the bag decreases below the lung pressure of the patient and a check valve prevents the exhalation gases from the patient from refilling the manual bag. When the pressure within the bag decreases below the pressure detected at the exhalation limb from the patient, the system begins the exhalation phase.

During the exhalation phase, an exhalation valve is opened to allow the patient to exhale until the exhalation pressure falls to the PEEP pressure. At the same time, the manual ventilation bag is being filled by the inhalation gas flow such that the manual ventilation bag can be utilized during the next ventilation cycle. The control system of the present invention begins the exhalation phase when the pressure within the manual bag falls below the exhalation pressure, thereby indicating that the manual bag has been released and needs to be refilled. The monitoring of the manual bag pressure and the exhalation pressure allows the system to automatically determine the beginning of the exhalation phase during the manual operation sequence.

BRIEF DESCRIPTION OF THE DRAWINGS

The drawings illustrate the best mode presently contemplated in carrying out the invention. In the drawings.

DETAILED DESCRIPTION OF THE INVENTION

Figure 1:
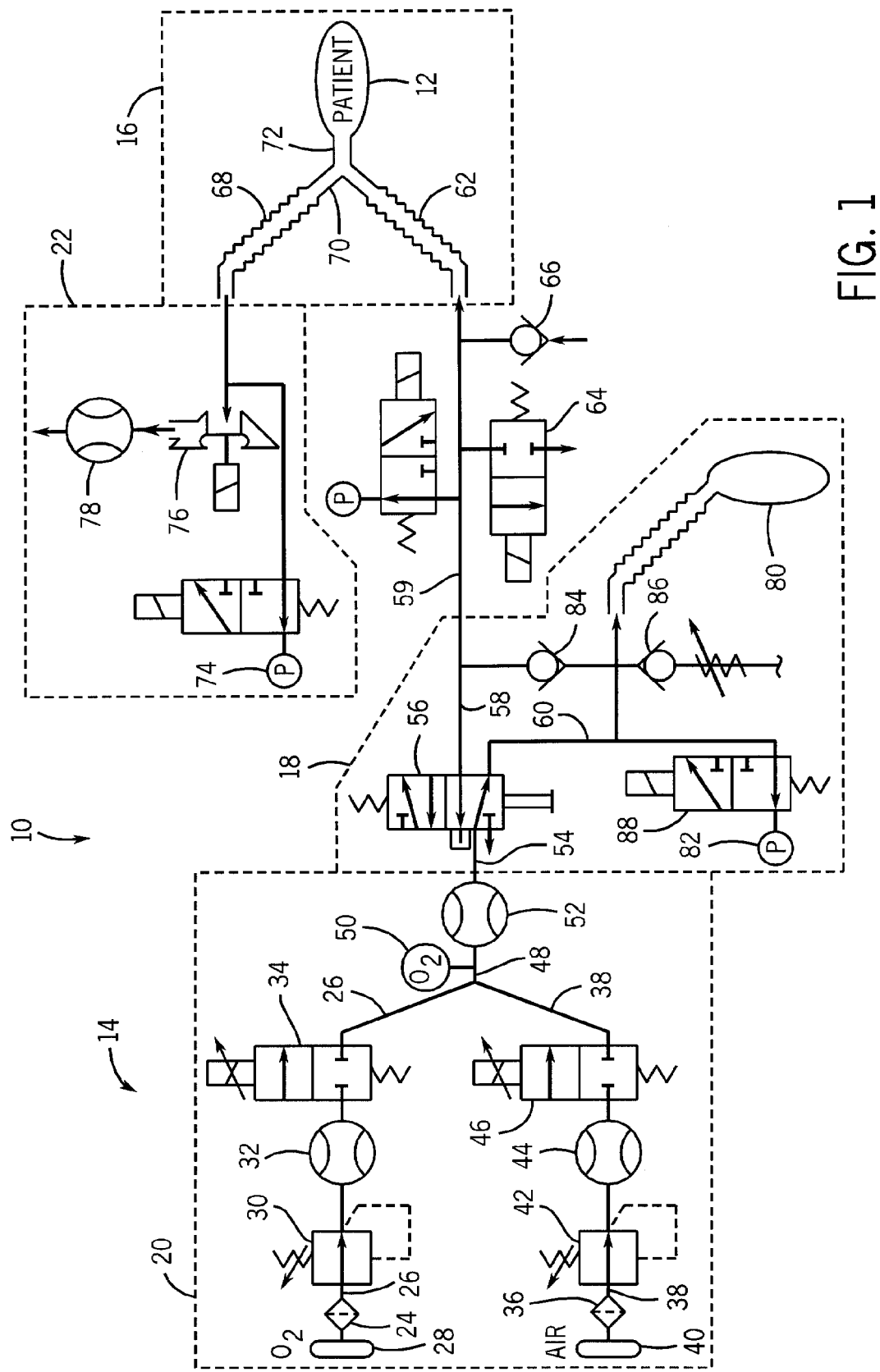
FIG. 1 illustrates an operational diagram of a ventilation system of the present invention including a manual ventilation system and an automatic ventilation system for use in an intensive care environment.

A ventilation system 10 is shown in FIG. 1 for providing an inhalation gas to a patient 12 for use in intensified breathing. The ventilation system of the present invention is particularly useful whenever the patient 12 is receiving intravenous anesthesia.

The ventilation system 10 generally includes a ventilator 14, a patient breathing circuit 16 and a manual ventilation circuit 18. The ventilator 14 generally comprises a gas supply system 20 and an exhalation control system 22 that are each controlled by a control system (not shown) of the ventilator 14.

As illustrated in FIG. 1, the gas supply system 20 includes a compressed oxygen interface 24, including a compressed oxygen conduit 26 connected to a compressed oxygen tank 28. The oxygen conduit 26 includes a pressure regulator 30, a gas flow sensor 32 and a flow control valve 34. The flow sensor 32 and flow control valve 34 are each coupled to the control system for the ventilator 14 such that the ventilator can control the flow rate of the oxygen.

Gas supply system 20 further includes a compressed air interface 36, including a compressed air conduit 38. The compressed air conduit 38 is coupled to a compressed air tank 40 and includes a pressure regulator 42, a gas flow sensor 44 and a flow control valve 46. Both the gas flow sensor 44 and the flow control valve 46 are coupled to the control system of the ventilator 14 for operational control of the air flow being supplied.

The operation of the flow control valves 34,46 are controlled by the control system of the ventilator 14 to produce the required gas mixture having the desired $O_2$ concentration and desired total flow rate. The control system utilizes the information provided by the gas flow sensors 32,44 to determine the flow rate and $O_2$ concentration of the inhalation gas. Preferably, the flow control valves 34,46 have proportional actuators to provide the relationship between gas flow rates and the valve control signal. In the embodiment of the invention illustrated, the gas flow sensors 32, 44 can be any type of state of the art sensor fitted to measure flow rates needed for the application, such as thermal or pressure difference flow sensors.

The flow of gases in the oxygen conduit 26 and the air conduit 38 combine within the supply conduit 48. The ventilator 14 includes a gas analyzer 50 to provide safety backup for oxygen concentration. As an example, if the control system for the ventilator 14 fails in providing the required gas mixture, the gas analyzer 50 will provide the required information to the control unit. The total gas flow within the supply conduit 48 is determined by a flow sensor 52. The flow sensor 52 provides additional safety backup against system flow sensing failures.

As illustrated in FIG. 1, the inhalation gas in the supply conduit 48 from the ventilator 14 is connected to an input 54 of a switching valve 56. The switching valve 56 is selectively movable between a first position in which the gas flow is provided directly to the gas conduit 58 and a second position in which the gas flow from the ventilator 14 is supplied to the connection line 60 of the manual ventilation circuit 18.

When the switching valve 56 is in the first position, the gas flow from the ventilator 14 is provided directly to inhalation conduit 59, which is coupled to the inhalation limb 62 of the patient breathing circuit 16. As illustrated, the inhalation conduit 59 includes an over pressure relief valve 64 and a spontaneous breathing valve 66 that provide safety against high and negative pressures within the inhalation conduit 59 leading to the inhalation limb 62.

The exhalation control system 22 of the ventilator 14 receives expired gases from the patient from the exhalation limb 68 of the patient Y-connector 70 that further includes the patient limb 72. The exhalation control system 22 includes an exhalation pressure sensor 74 that monitors the pressure within the exhalation limb 68 of the patient breathing circuit 16. The control unit for the ventilation system 10 controls the opening and closing of an exhalation valve 76. The exhalation valve 76 can be opened to vent exhalation gases from the patient, through a flow sensor 78, to atmosphere. The opening and closing of the exhalation valve 76 is controlled during expiration to maintain the partial end-expiratory pressure (PEEP) within the patient.

As described previously, the position of the switching valve 56 controls whether the ventilation system 10 is operating in a manual mode or in an auto-ventilation mode. Preferably, the switching valve 56 may be electrically or pneumatically actuated. However, the switching valve 56 may also have a direct access actuator button or lever for immediate manual access as an alternative. The switching valve 56 provides a gas flow path either to a manual bag 80 or directly to the patient through the gas conduit 58 and inhalation conduit 59.

When the switching valve 56 is in the manual position, the gas flow present at the input 54 is directed toward the manual bag 80 through the connection line 60. A bag pressure sensor 82 monitors the pressure within the manual bag 80 and provides this information to the control system for the entire ventilation system 10. The connection line 60 interfaces to an inhalation check valve 84 and an optional manually adjustable pressure limiting (APL) valve 86. The pressure sensor 82 can be optionally equipped with a calibration valve 88 to determine the sensor output respective to zero pressure difference to atmosphere.

The operation of the ventilation system 10 during manual ventilation will now be described. During manual ventilation, the switching valve 56 is set on the manual ventilation position to allow inhalation gas to flow from the input 54 through the connection line 60 into the manual bag 80. The inhalation gas flow and mixture is controlled with the flow control valves 34, 46. Pressure sensor 82 monitors the pressure within the manual bag 80 and, when the pressure within the manual bag reaches the PEEP value, which is an ordinary setting for the ventilator, or the minimum bag pressure whichever is larger, the flow control valves 34, 36 are closed to prevent further inflation of the bag 80. When manual ventilation of the patient is required, the manual bag 80 is squeezed, causing the pressure within the bag to rise over the PEEP pressure, which represents the pressure within the patient's lungs at the end of expiration. Since the pressure within the manual bag 80 exceeds the PEEP pressure, the inhalation gases within the manual bag 80 are delivered to the patient through the inhalation conduit 59 and into the inhalation limb 62. The relief valve 64 assures that the pressure of the gases flowing into the patient 12 do not exceed a selected safety limit value.

When the manual ventilation bag 80 is released, the pressure within the bag decreases below the lung pressure, measured by the exhalation pressure sensor 74, which was increased during the manual inhalation. The check valve 84 automatically closes to prevent the flow of exhalation gases from the patient 12 back into the manual bag 80.

The pressure within the manual bag decreases under the PEEP pressure after the manually-induced inhalation. The manual bag pressure sensor 82 signals this pressure to the control system, which then opens the flow control valves 34, 46 to refill the manual bag 80 with the inhalation gas mixture for the next inspiration.

When the manual bag 80 is released after manual deflation, the pressure within the manual bag 80 decreases below the pressure in the exhalation limb 68, as detected by the exhalation pressure sensor 74. These circumstances signal to the control system that inspiration is stopped. As a response to this, the controller of the ventilation system 10 opens the exhalation valve 76 to allow breathing gases from the patient 12 to be exhaled to atmosphere. The exhalation valve 76 remains open until the exhalation pressure measured by the exhalation pressure sensor 74 reaches the PEEP pressure. Once the exhalation pressure sensed by the pressure sensor 74 reaches the PEEP pressure, the control system of the ventilator 10 closes the exhalation valve 76 to maintain the PEEP pressure for the patient 12. As described above, the control system of the ventilator identifies the beginning of the exhalation phase when the exhalation pressure sensed by the exhalation pressure sensor 74 is greater than the bag pressure, which indicates the release of the bag after manual deflation of the bag.

As discussed previously, after the manual ventilation bag has been deflated, the manual ventilation bag 80 is re-inflated by opening the flow control valves 34, 36 such that the manual ventilation bag 80 can be used during the next breathing cycle. A manual bag pressure decrease below the larger of PEEP or minimum bag pressure signals the control system to refill the manual bag by opening the flow control valves 34, 46.

Figure 2:
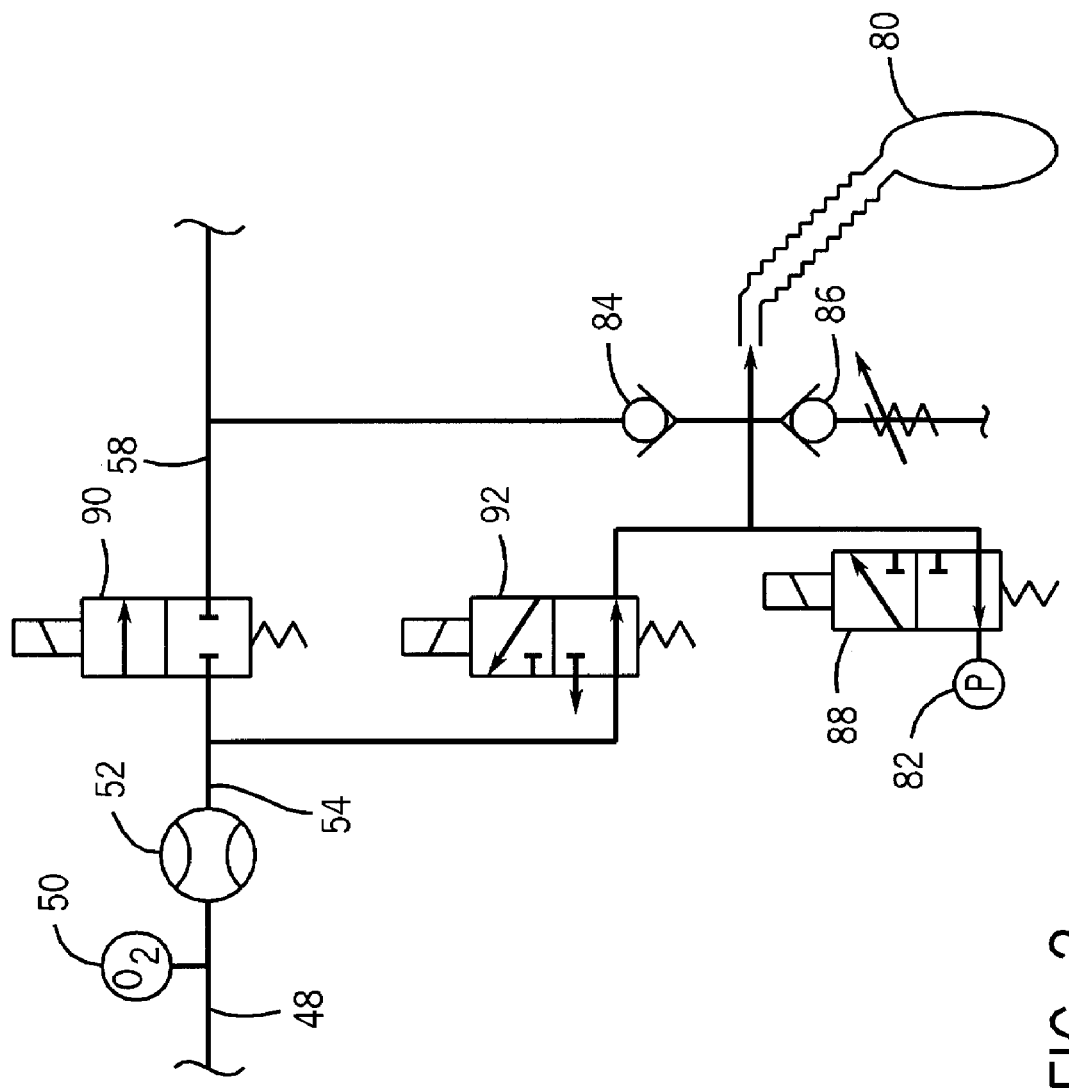
FIG. 2 is an operational diagram of an alternative solution for directing the mixed gases to either the patient or the manual ventilation system.

FIG. 2 illustrates an alternate embodiment for the switching valve 56 shown in FIG. 1. In FIG. 2, the switching valve has been replaced by the combination of an auto-ventilation valve 90 and a manual ventilation valve 92. In the embodiment of the invention illustrated, the auto-ventilation valve 90 is a type 2/2 valve providing open/closed functionality for the auto-ventilation. The manual ventilation valve 92 is preferably a 3/2 type valve where the third port is used to open the manual bag 80 to atmosphere for pressure relief on auto-ventilation.

When the ventilation system needs to be operated in automatic mode, the auto-ventilation valve 90 is opened and the manual ventilation valve 92 is closed. Likewise, when manual ventilation is selected, the auto-ventilation valve 90 is closed while the manual ventilation valve 92 is opened. It is important to note that at no time will both the auto-ventilation valve 90 and the manual ventilation valve 92 be simultaneously open.

We claim:

1. A ventilation system for intensified breathing of a patient, the system comprising:
   a gas supply system for providing a supply of inhalation gas for breathing by the patient;
   an inhalation conduit positioned to supply the inhalation gas to the patient;
   a single switching valve operable in a first state and a second state and positioned to receive the inhalation gas from the gas supply system, the switching valve being positionable in the first state to divert the inhalation gas to the inhalation conduit;
   a manual ventilation bag positioned to receive the inhalation gas directly from the switching valve when the switching valve is in the second state, the manual ventilation bag being selectively inflatable with the inhalation gas when the switching valve is in the second state, wherein upon compression, the manual ventilation bag supplies the inhalation gases to the inhalation conduit;
   a bag pressure sensor positioned to detect the pressure in the manual ventilation bag, wherein when the switching valve is in the second state, the gas supply system supplies the inhalation gas to the manual ventilation bag when the pressure in the manual ventilation bag is below a minimum gas pressure; and
   an exhalation conduit for receiving exhaled gases expired from the patient, wherein the gas supply system includes a first flow control valve coupled to a supply of oxygen and operable to regulate the flow of oxygen to the switching valve and a second flow control valve coupled to a supply of air and operable to regulate the flow of air to the switching valve.

2. The system of claim 1 wherein
   the first and second flow control valves are selectively opened to supply the inhalation gas to the manual ventilation bag when the switching valve is in the second state and the pressure in the manual ventilation bag is below the minimum gas pressure for the patient.

3. The system of claim 2 further comprising:
an exhalation valve positioned in the exhalation conduit to selectively control the exhalation of breathing gases from the patient; and
an exhalation pressure sensor operable to detect the pressure in the exhalation conduit;
wherein the exhalation valve is movable to an open position to permit the exhalation of breathing gases from the patient when the detected pressure in the manual ventilation bag is less than the detected pressure in the exhalation conduit.

4. The system of claim 3 wherein the exhalation valve is movable to the open position only when the exhalation pressure in the exhalation conduit is greater than the PEEP pressure for the patient.

5. The system of claim 2 wherein the first and second flow control valves are closed to restrict the supply of inhalation gas to the manual ventilation bag when the detected pressure in the manual ventilation bag is greater than a minimum bag pressure.

6. The system of claim 1 further comprising a check valve positioned between the inhalation conduit and the manual ventilation bag to prevent the flow of exhalation gases from the patient to the manual ventilation bag.

7. A method of controlling the delivery of an inhalation gas to a patient, the method comprising the steps of:
providing a patient circuit having an inhalation conduit for delivering the inhalation gas to the patient and an exhalation conduit for receiving exhaled gases from the patient;
providing a gas supply system selectively operable to control the supply of the inhalation gas;
positioning a single switching valve to receive the supply of inhalation gas, the switching valve being positionable in a first state and a second state;
selectively moving the switching valve to the first state to divert the inhalation gas directly to the inhalation conduit to provide auto-ventilation;
selectively moving the switching valve to the second state to divert the inhalation gas directly to a manual ventilation bag for manual ventilation of the patient;
manually deflating the manual ventilation bag to supply the inhalation gas from the manual ventilation bag to the inhalation conduit when the switching valve is in the second state;
monitoring the pressure in the manual ventilation bag; and
selectively opening at least one flow control valve of the gas supply system to provide the inhalation gas to fill the manual ventilation bag when the switching valve is in the second state and the pressure in the manual ventilation bag is below a minimum bag pressure.

8. The method of claim 7 further comprising the step of opening an exhalation valve coupled to the exhalation conduit to permit the exhalation of gas from the patient when the pressure in the exhalation conduit exceeds the pressure in the manual ventilation bag and exceeds a PEEP pressure for the patient.

9. The method of claim 8 further comprising the step of closing the exhalation valve to prevent the exhalation of gas from the patient when the pressure in the exhalation conduit falls below the PEEP pressure.

10. The method of claim 8 wherein the gas supply system includes an oxygen flow control valve coupled to a supply of oxygen and an air flow control valve coupled to a supply of air, wherein the method further comprises the steps of:
selectively opening the oxygen flow control valve and the air flow control valve to provide the inhalation of gas to the switching valve.

* * * * *